(12) United States Patent
Xu

(10) Patent No.: US 9,102,650 B2
(45) Date of Patent: Aug. 11, 2015

(54) SYNTHESIS OF NEW ANTI-INFLAMMATORY COMPOUND

(71) Applicant: Yong Xu, San Diego, CA (US)

(72) Inventor: Yong Xu, San Diego, CA (US)

( * ) Notice: Subject to any disclaimer, the term of this patent is extended or adjusted under 35 U.S.C. 154(b) by 0 days.

(21) Appl. No.: 14/454,761

(22) Filed: Aug. 8, 2014

(65) Prior Publication Data

US 2015/0112087 A1    Apr. 23, 2015

(51) Int. Cl.

| | |
|---|---|
| C07D 317/36 | (2006.01) |
| C07D 309/10 | (2006.01) |
| C07D 493/04 | (2006.01) |
| C07C 67/307 | (2006.01) |
| C07C 67/343 | (2006.01) |
| C07C 2/54 | (2006.01) |
| C07C 51/09 | (2006.01) |
| C07C 17/16 | (2006.01) |
| C07C 29/147 | (2006.01) |
| C07F 17/00 | (2006.01) |
| C07F 9/40 | (2006.01) |

(52) U.S. Cl.
CPC ............... *C07D 317/36* (2013.01); *C07C 2/54* (2013.01); *C07C 17/16* (2013.01); *C07C 29/147* (2013.01); *C07C 51/09* (2013.01); *C07C 67/307* (2013.01); *C07C 67/343* (2013.01); *C07D 309/10* (2013.01); *C07D 493/04* (2013.01); *C07F 9/4018* (2013.01); *C07F 17/00* (2013.01)

(58) Field of Classification Search
CPC combination set(s) only.
See application file for complete search history.

(56) References Cited

PUBLICATIONS

Madara et al., caplus an 1995:435841.*

* cited by examiner

*Primary Examiner* — Sun Jae Yoo
(74) *Attorney, Agent, or Firm* — Houtteman Law LLC

(57) ABSTRACT

According to embodiments of present disclosure, a method to produce a compound of Formula 19 is provided. Using this method, the compound of Formula 19 may be produced effectively.

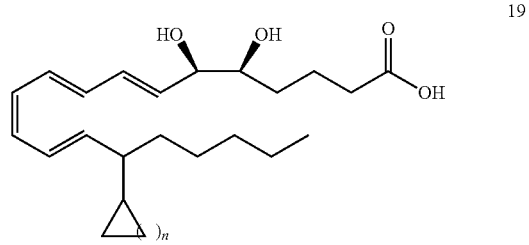

1 Claim, No Drawings

SYNTHESIS OF NEW ANTI-INFLAMMATORY COMPOUND

FIELD

The present invention relates generally to the synthesis of Lipoxin derivate. In particular it relates to the preparation of Lipoxin derivate and intermediates for the preparation of Lipoxin derivate.

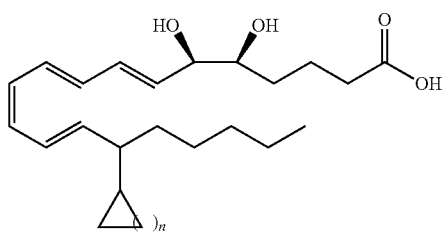

BACKGROUND

Lipoxins are a series of anti-inflammatory mediators. Lipoxins are short lived endogenously produced nonclassic eicosanoids whose appearance in inflammation signals the resolution of inflammation. They are abbreviated as LX, an acronym for lipoxygenase (LO) interaction products. At present two lipoxins have been identified; lipoxin A4 (LXA4) and lipoxin B4 (LXB4).

Lipoxins were first described by Serhan, Hamberg and Samuelsson in 1984. They reported that the lipoxins stimulated superoxide anion ($O^{2-}$) generation and degranulation at submicromolar concentrations—as potent as LTB4.

Lipoxins, as well as certain peptides, are high affinity ligands for the lipoxin A4 receptor (LXA4R), which was first identified based on sequence homology as the formyl peptide receptor like receptor (FPRL1). Lipoxin signaling through the LXA4R inhibits chemotaxis, transmigration, superoxide generation and NF-κB activation. Conversely, peptide signaling through the same receptor, in vitro, has been shown to stimulate chemotaxis of polymorphonuclear cells (PMNs) and calcium mobilization. The peptides that have ALXR affinity tend to be signals for leukocyte migration and subsequent phagocytosis such as acute phase proteins, bacterial peptides, HIV envelope proteins and neurotoxic peptides. Similarly to the leukotrienes, LXA4 will form the cysteinyl-lipoxins LXC4, LXD4 and LXE4. At subnanomolar concentrations, LXA4 and LXB4 inhibit leukotriene-stimulated interactions of human neutrophils and endothelial cells. Lipoxins are high affinity antagonists to the cysteinyl leukotriene receptor type 1 (CysLT1) to which several leukotrienes (LTC4, LTD4 and LTE4) mediate their smooth muscle contraction and eosinophil chemotactic effects. The CysLT1 receptor is also the site of action for the asthma drug montelukast.

SUMMARY

The present disclosure directs to solve at least one of the problems existing in the prior art to at least some extent. Thus, one purpose of the present disclosure is to provide a method to effectively produce a compound of Formula 19 and the intermediate thereof.

In the first aspect of the present invention, a method for producing a compound of Formula 19 is provided, and the method comprises:

contacting a ethyl propiolate with a lithium bromide base in the presence of HOAC in $CH_3CN$ to obtain the compound of Formula 2;

contacting a compound of Formula 3 with n-Buli bromocyclane in THF to obtain a compound of Formula 4;

contacting the compound of Formula 4 with $HZrCp_2Cl$ in THF to obtain a compound of Formula 5;

contacting the compound of Formula 2 with the compound of Formula 4 in the presence of $Pd(PPH_3)_2Cl_2$, DIBAH and $ZnCl_2$ to obtain a compound of Formula 6;

contacting the compound of Formula 6 with DIBAL in DCM to obtain a compound of Formula 7;

contacting the compound of Formula 7 with $CBr_4$, $PPh_3$, imidazole in DCM to obtain a compound of Formula 8;

contacting the compound of Formula 8 with $P(OMe)_3$ in $CH_3CN$ to obtain a compound of Formula 9;

contacting the compound of Formula 10 with acetyl chloride in MeOH under room temperature to obtain a compound of formula 11;

contacting compound of Formula 11 with CDI in $CH_3CN$ under a condition of refluxing to obtain a compound of Formula 12;

contacting the compound of Formula 12 with HCL in a mixture of Dioxane and water under a condition of refluxing to obtain a compound of Formula 13, wherein the volume ratio of Dioxane to water is about 3:1;

contacting the compound of Formula 13 with $Ph_3PCHCO_2$ and Benzolic acid in toluene under a condition of refluxing to obtain a compound of Formula 14;

contacting the compound of Formula 14 with $H_2$ in the presence of Pd/C in EtOH to obtain a compound of Formula 15;

contacting the compound of Formula 15 with DCC, and $Cl_2CHCOOH$ to obtain a compound of Formula 16;

contacting the compound of Formula 16 with $Ph3P=CHCHO$ in DCM to obtain a compound of Formula 17;

contacting the compound of Formula 17 with the compound of Formula 9 in the presence of LDA and HMPA in THF to obtain a compound of Formula 18;

contacting the compound of Formula 18 with NaOH in MeOH to obtain the compound of Formula 19

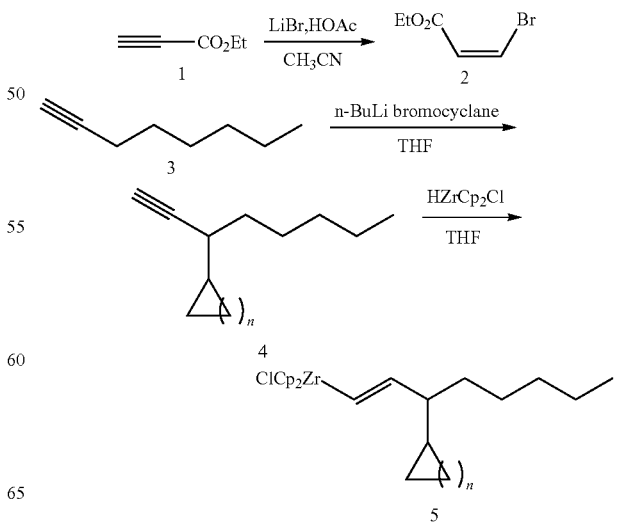

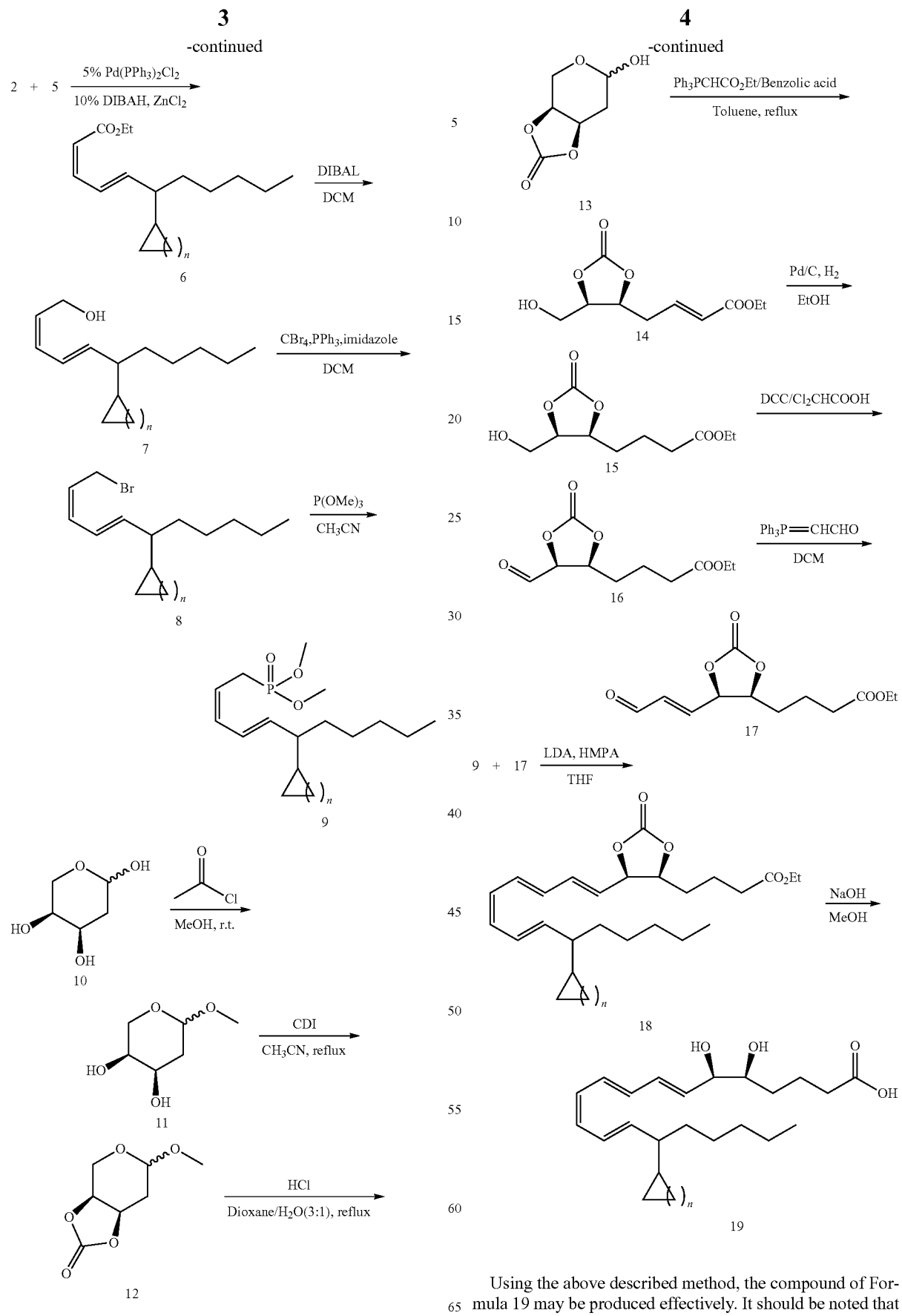
Using the above described method, the compound of Formula 19 may be produced effectively. It should be noted that in the present disclosure the expression of "compound of Formula N" may be also interchangeable with the expression of "Compound N", and the term N means the number of the compound. For example, compound 19 is interchangeable with "compound of Formula 19".

In another aspect of present disclosure, there is provide a method of producing a compound of Formula 6, comprising contacting a compound of Formula 2 with a Bis(triphenylphosphine) palladium(II) chloride and diisobutylaluminum hydride to obtain the compound of Formula 6, wherein n is an integer between 1 to 5

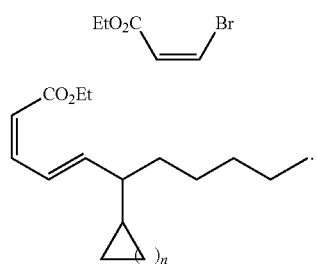

In some embodiments of present disclosure, wherein the contacting is performed in THF.

In some embodiments of present disclosure, is performed in the presence of in zinc chloride.

In some embodiments of present disclosure, Bis(triphenylphosphine) palladium(II) chloride is about 2% to about 8% of that of compound of Formula 2.

In some embodiments of present disclosure, the contacting is carried out under a temperature ranging from room temperature to about reflux temperature.

In some embodiments of present disclosure, further comprising contacting the compound of Formula 6 with DIBAL-D in DCM to obtain a compound of Formula 7, wherein n is an integer between 1 to 5

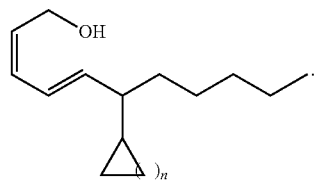

In some embodiments of present disclosure, the concentration of DIBAL-D is 1.2M to 2.0M.

In some embodiments of present disclosure, the compound of Formula 2 is produced by the step of:
contacting a ethyl propiolate with a lithium bromide base to obtain the compound of Formula 2

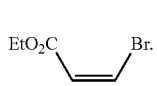

In some embodiments of present disclosure, the contacting of ethyl propiolate with lithium bromide base is performed in a solvent comprising acetic acid and acetonitrile, and the volume ratio of acetic acid to acetonitrile is 1:2~2:1.

In some embodiments of present disclosure, the contacting of ethyl propiolate with lithium bromide base is performed under a temperature ranging from about 40° C. to about a reflux temperature.

In another aspect of present disclosure, there is provide a method of produce a compound of Formula 14 comprising: contacting a compound of Formula 13 with Ethyl (triphenylphosphoranylidene)acetate and enzolic acid to obtain the compound of Formula 14

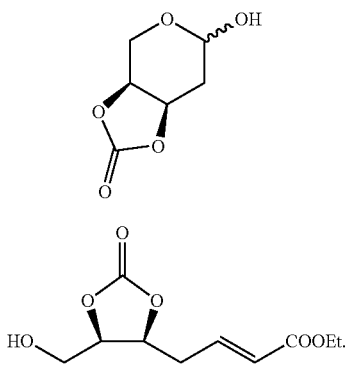

In some embodiments of present disclosure, the contacting is performed under a temperature ranging from room temperature to about reflux temperature.

In some embodiments of present disclosure, the contacting is performed in toluene.

In another aspect of present disclosure, there is provided a method of producing a compound of Formula 18 comprising: contacting a compound of Formula 9 with a compound of Formula 17 to obtain the compound of Formula 18, wherein n is an integer between 1 to 5

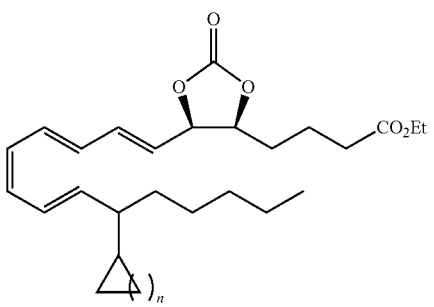

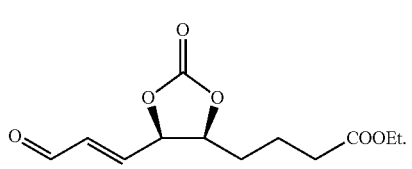

In some embodiments of present disclosure, the contacting is performed in the presence of a base, wherein the base is selected from a group consisting of LDA, n-BuLi, and NaH.

In some embodiments of present disclosure, the concentration of the base is about 1.1M to about 1.5M.
In some embodiments of present disclosure, the contacting is performed under a temperature ranging from about −78° C. to room temperature.
All in above the following scheme shows a process for preparation of Lipoxin derivate as described herein (n=1, 2, 3, 4, 5).
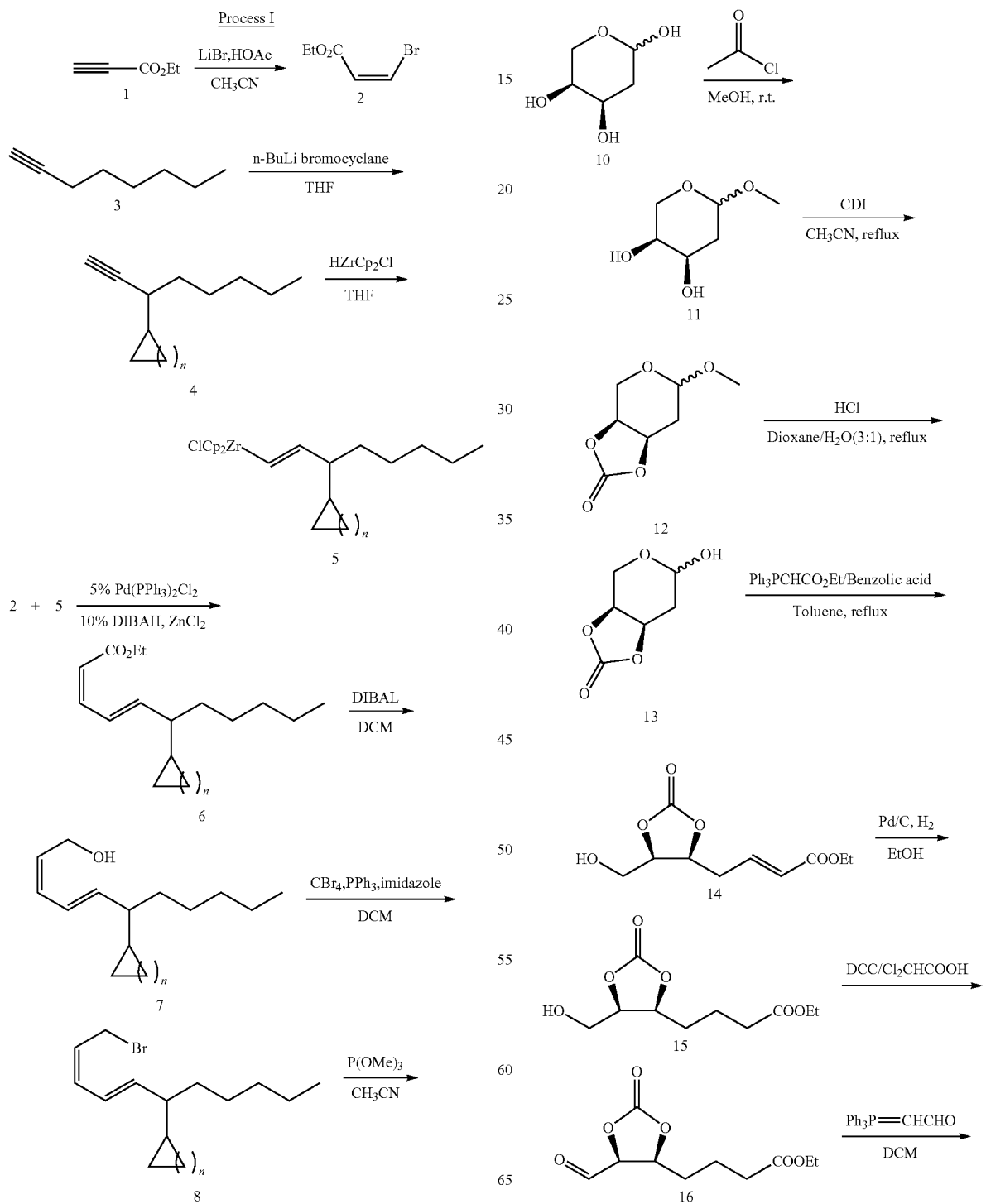

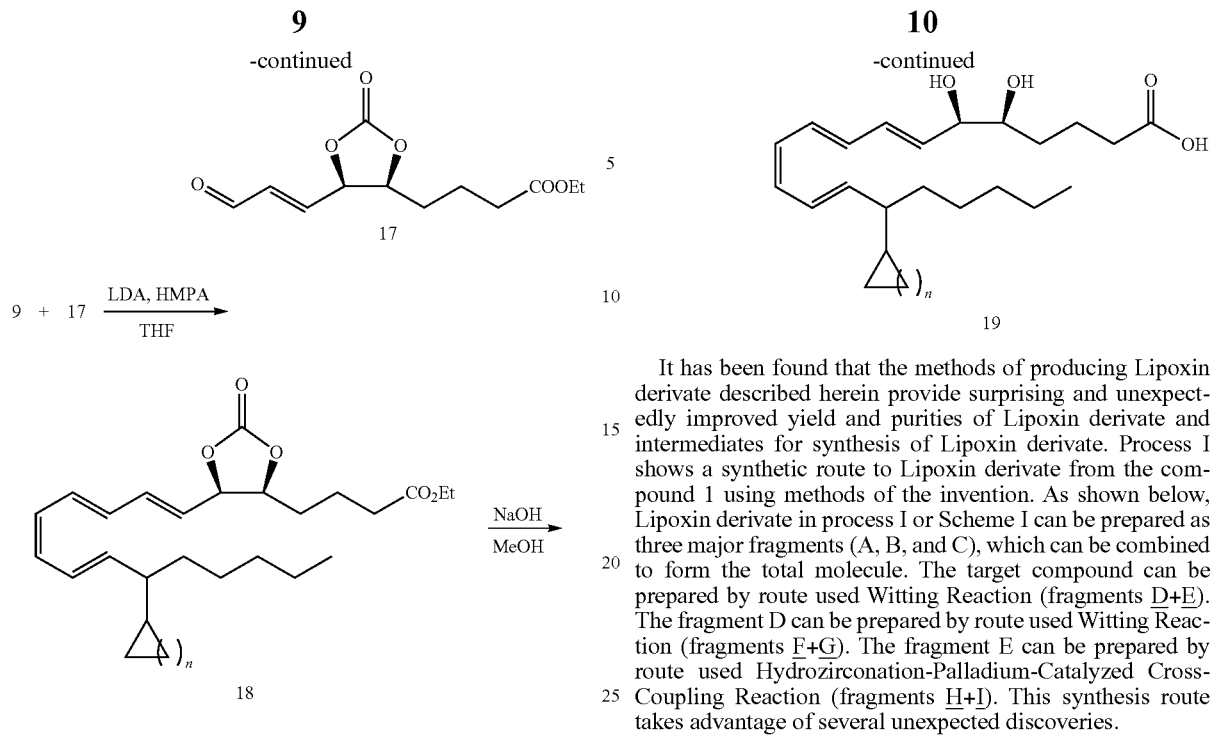

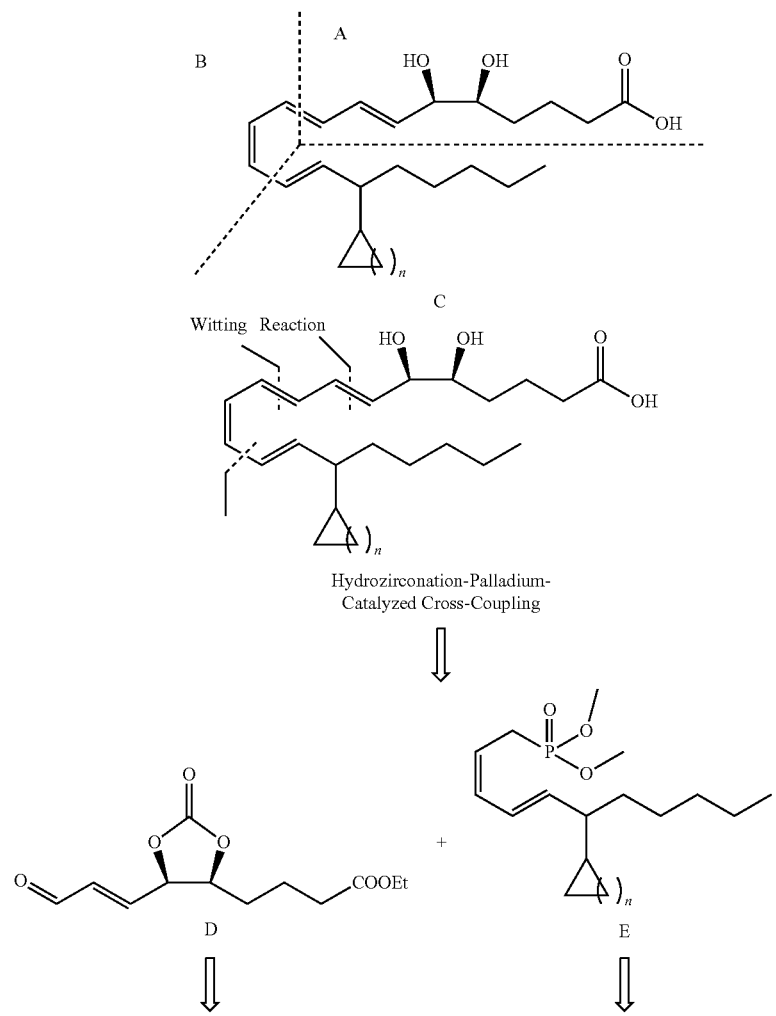

It has been found that the methods of producing Lipoxin derivate described herein provide surprising and unexpectedly improved yield and purities of Lipoxin derivate and intermediates for synthesis of Lipoxin derivate. Process I shows a synthetic route to Lipoxin derivate from the compound 1 using methods of the invention. As shown below, Lipoxin derivate in process I or Scheme I can be prepared as three major fragments (A, B, and C), which can be combined to form the total molecule. The target compound can be prepared by route used Witting Reaction (fragments D+E). The fragment D can be prepared by route used Witting Reaction (fragments F+G). The fragment E can be prepared by route used Hydrozirconation-Palladium-Catalyzed Cross-Coupling Reaction (fragments H+I). This synthesis route takes advantage of several unexpected discoveries.

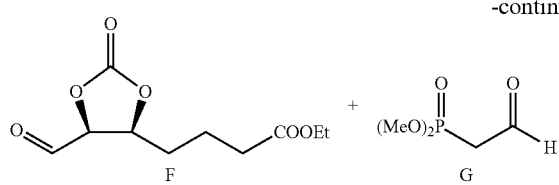

F

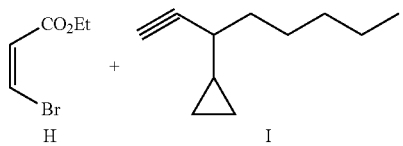

G

H                I

The total synthesis of process routes of the target product are mild reaction conditions, less environmental pollution, and reliable synthesis process. The synthesis process of Lipoxin derivate are mature reactions. It has been found that the product obtained from the present method improves not only the yield and purity of the compound of intermediates, but also the yield an purities of the final product, Lipoxin derivate, compared to the use of other methods.

EXAMPLE

The following abbreviations are used in the Examples and throughout this disclosure.
CDI 1,1'-Carbonyldiimidazole
DCM Dichloromethane
DCC Dicyclohexylcarbodiimide
DIBAL Diisobutylaluminium hydride
GC Gas Chromatography
LDA Lithium diisopropylamide
n-BuLi n-Butyllithium
$PBr_3$ Phosphorus tribromide
THF Tetrahydrofuran Synthesis of (5S,6R,7E,9E,11Z,13E)-15-cyclopropyl-5,6-dihydroxyicosa-7,9,11,13-tetraenoic acid Step1: Ethyl 3-bromoacrylate

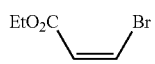

2

A mixture contain ethyl propiolate (5.0 g, 51 mmol) and lithium bromide (4.3 g, 51 mmol) in acetic acid (10 mL) and acetonitrile (10 mL) was stirred for 2 hours at 60° C. Then, water (50 mL) was poured into the mixture, and extracted with ethyl acetate. The organic phase was dried over $Na_2SO_4$, the sulfate was filtered off and concentrated to obtain 8.2 g Compound 2, yield: 91%. GC/MS: 177;

1H-NMR (DMSO-d6): δ=6.80 (d, J=10.8 Hz, 1H), 6.62 (d, J=10.8 Hz, 1H), 1.40 (q, 2H), 0.85 (t, 3H).

Step2: tert-butyldimethyl(3-methyloct-1-yn-3-yloxy)silane

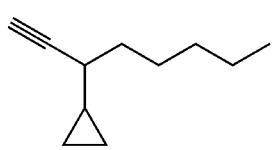

4

A mixture of oct-1-yne (5.5 g, 50 mmol) in tetrahydrofuran (60 mL), and cooled by dry ice-acetone to −78° C. Then, n-butyllithium (60 mmol) was added into the mixture. The mixture was stirred for 30 mins at this temperature, then, bromocyclopropane (6.6 g, 55 mmol) was added. The mixture was stirred at room temperature for 4 hours. After complication of the reaction, the mixture was quenched by ammonium chloride solution, water (80 mL) was poured into the mixture, and extracted with ethyl acetate. The organic phase was dried over $Na_2SO_4$, the sulfate was filtered off and concentrated to obtain crude product and purified by flash chromatography to obtain 5.3 g Compound 4, yield: 71%.

1H-NMR (DMSO-d6): δ=3.01 (s, 1H), 2.65 (q, 1H), 1.25-1.4 (m, 8H), 0.90 (t, 3H), 0.2-0.3 (m, 4H), 0.28 (s, 1H).

Step3: Synthesis of Compound 5

5

A mixture of compound 4 (1.5 g, 10 mmol) and $HZrCp_2Cl$ (3.08 g, 12 mmol) in THF (50 mL), and the mixture was stirred at room temperature for 12 hours. Water (60 mL) was poured into the mixture, and extracted with ethyl acetate. The organic phase was washed with brine and dried over $Na_2SO_4$, the sulfate was filtered off and concentrated to obtain crude product compound 5 for next step without purification.

Step4: Synthesis of Compound 6

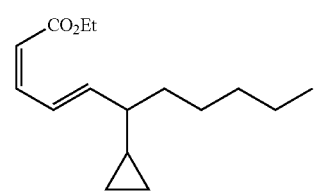

6

A mixture of compound 5 (3.96 g, 9.5 mmol) and compound 2 (1.68 g, 9.5 mmol) in THF (50 mL), then the Bis(triphenylphosphine)palladium(II) chloride (5%, 330 mg), diisobutylaluminum hydride (10%) and a trace of $ZnCl_2$ were added to the mixture. The mixture was stirred under nitrogen reflux for 12 hours. Water (100 mL) was poured into the mixture, and extracted with ethyl acetate. The organic phase was washed with aq saturated $NaHCO_3$, brine and dried over $Na_2SO_4$, the sulfate was filtered off and concentrated to obtain crude product, and purified with flash chromatography to obtain 1.6 g compound 6, yield 64% in two steps.

Step5: Synthesis of Compound 7

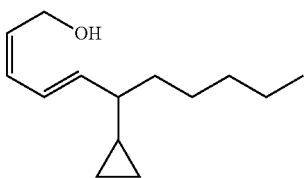

A 250-mL round-bottom flask was charged with a solution of compound 6 (2.5 g, 10 mmol) in DCM (50 mL) and then cooled with a dry ice-acetone bath. A 50-mL solution of 1.5 M DIBAL-D in DCM was added over 30 min and then the solution was allowed to warm to 0° C. over 2 h. The reaction was quenched by slowly adding 2 M $NH_4Cl$ (aq) solution until gas evolution stopped. The reaction mixture became thick with gelatinous material. This was separated from the DCM, dissolved with 2 M $H_2SO_4$, and then extracted with DCM (4×20 mL). Organic layers were combined, then washed ($H_2O$, 5% $NaHCO_3$, brine), and dried with $MgSO_4$, and solvent was removed. The crude product was purified by column chromatography to give 1.8 g compound 7, yield 72%.

1H-NMR (DMSO-d6): δ=6.28 (m, 1H), 6.25 (m, 1H), 5.78 (m, 2H), 5.68 (m, 1H), 2.15 (m, 1H), 1.20-1.30 (m, 8H), 0.90 (t, 3H), 0.3-0.5 (m, 5H).

Step6: Synthesis of Compound 8

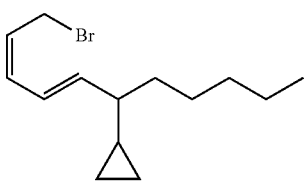

A 50 mL round-bottom flask was charged with $PBr_3$ (1.23 g, 4.52 mmol) and then cooled with dry ice-acetone. A solution of compound 7 (2.24 g, 10.8 mmol) in $Et_2O$ (15 mL) was added over 20 min. The solution was allowed to gradually warm to −25° C. during the next 30 min, at which point the cooling bath was removed. It was stirred an additional 3.5 h and then poured into separatory funnel containing ice and solid $NaHCO_3$ (2.5 g). The flask was rinsed with $Et_2O$ (2×15 mL) and the rinses were added to the separatory funnel. The mixture was shaken until the ice had melted and then separated. The aqueous layer was extracted with $Et_2O$ (2×15 mL), and the organic layers were combined, washed with brine, and dried with $Na_2SO_4$. A small aliquot was removed and concentrated to obtain crude product compound 8 for next step without further purification.

LC/MS: [M+H]=375

Step7: Synthesis of Compound 9

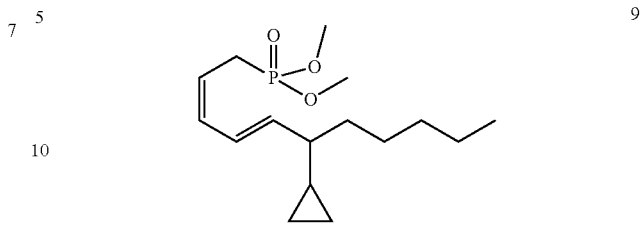

The compound 8 (1.78 g, 6.6 mmol) was dissolved in acetonitrile (10 mL), and the trimethyl phosphite (900 mg, 7.26 mmol) was added into the solution. The mixture was stirred under nitrogen at room temperature overnight. After complication of the reaction the water (60 mL) was poured into the solution, and extracted with $NaHCO_3$ (2.5 g). The flask was rinsed with $Et_2O$ (2×15 mL) and the rinses were added to the separatory funnel. The mixture was shaken until the ice had melted and then separated. The aqueous layer was extracted with ethyl acetate. The organic phase was washed with aq saturated $NaHCO_3$, brine and dried over $Na_2SO_4$, the sulfate was filtered off and concentrated to obtain crude product, and purified with flash chromatography to obtain 1.56 g compound 9, yield: 78%

Step8:
(3S,4R)-6-methoxytetrahydro-2H-pyran-3,4-diol

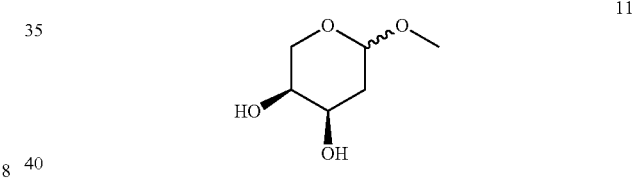

The (4R,5S)-tetrahydro-2H-pyran-2,4,5-triol (2.68 g, 20 mmol) was dissolved in MeOH (30 mL) and cooled by ice-bath, acetyl chloride (1.63 g, 21 mmol) was dropped into the solution. After addition, the mixture was stirred at room temperature for 3 hours. After complication, the mixture was pureed into water (100 mL), and extracted with ethyl acetate. The organic phase was washed with aq saturated $NaHCO_3$, brine and dried over $Na_2SO_4$, the sulfate was filtered off and concentrated to obtain product, and purified with flash chromatography to obtain 2.2 g compound 11, yield: 74%

1H-NMR (DMSO-d6): δ=4.86 (m, 1H), 3.86 (s, 2H), 3.34 (s, 3H), 3.25 (m, 2H), 2.68 (s, 2H), 1.86 (m, 2H).

Step9: Synthesis of compound 12

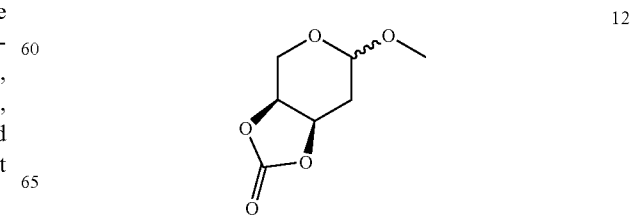

The compound 11 (2.2 g, 14.8 mmol) was dissolved in acetonitrile (20 mL) and 1,1'-Carbonyldiimidazole (2.4 g, 14.8 mmol) was added into the solution. The mixture was stirred reflux for 6 hours. After complication, the mixture was pureed into water (100 mL), and extracted with ethyl acetate. The organic phase was washed with 1N HCl (20 mL), brine and dried over Na₂SO₄, the sulfate was filtered off and concentrated to obtain product 2.23 g for next step.

Step10: Synthesis of compound 13

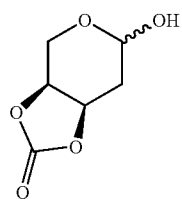

13

The compound 12 (2.23 g, 12.8 mmol) was dissolved in a mixture solution (20 mL, Dioxane/H₂O=3:1), 4N HCl (10 mL) was added into the mixture. Then, the mixture was stirred reflux for 5 hours. After complication, the mixture was concentrated to obtain 2.0 g compound 13 for next step.

Step11: (E)-ethyl 4-((4S,5R)-5-(hydroxymethyl)-2-oxo-1,3-dioxolan-4-yl)but-2-enoate

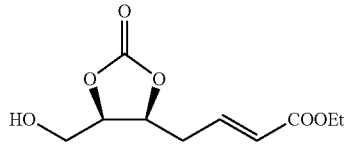

14

The compound 13 (3.2 g, 20 mmol) was dissolved in toluene (30 mL) and Benzolic acid (20 mmol), Ethyl (triphenylphosphoranylidene)acetate (7.3 g, 21 mmol) were added into the solution. The mixture was stirred reflux overnight. After complication, the mixture was concentrated to obtain oily product, and dissolved in DCM (50 mL), washed with (H₂O, 5% NaHCO₃, brine), and dried with MgSO₄, and solvent was removed. The crude product was purified by column chromatography to give 2.86 g compound 14, yield 62%.

1H-NMR (DMSO-d6): δ=6.86 (m, 1H), 5.85 (d, 1H), 4.23-4.26 (m, 2H), 4.04 (t, 2H), 3.98 (m, 2H), 2.52 (m, 2H), 1.66 (t, 3H).

Step12: ethyl 4-((4S,5R)-5-(hydroxymethyl)-2-oxo-1,3-dioxolan-4-yl)butanoate

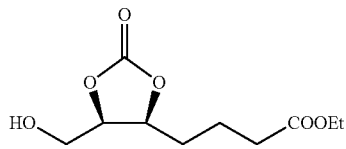

15

The compound 14 (2.0 g, 8.7 mmol) was dissolved in EtOH (15 mL), Pd/C (10%, 200 mg) was added. The mixture was stirred under hydrogen (2 tams) at room temperature overnight. Then, the solution was filtered and concentrated to obtain 1.86 g compound 15 for next step.

Step13: ethyl 4-((4S,5S)-5-formyl-2-oxo-1,3-dioxolan-4-yl)butanoate

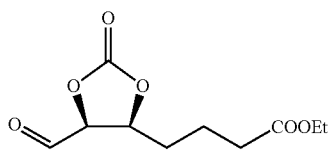

16

The compound 15 (3.0 g, 12.9 mmol) was dissolved in dichloroacetic acid (25 mL), dicyclohexylcarbodiimide (2.92 g, 14.1 mmol) was added. The mixture was stirred at room temperature 8 hours. Then, the solution was filtered and concentrated, and dissolved in DCM (60 mL), washed with (H₂O, 5% NaHCO₃, brine), and dried with MgSO₄, and solvent was removed to obtain crude product 2.8 g for next step.

Step14: ethyl 4-((4S,5R)-2-oxo-5-((E)-3-oxoprop-1-enyl)-1,3-dioxolan-4-yl)butanoate

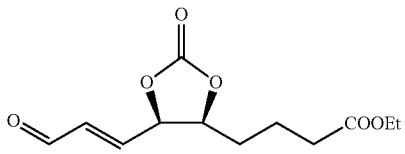

17

The compound 16 (2.5 g, 10.8 mmol) was dissolved in dichloromethane (30 mL), Ph₃P=CHCHO (3.28 g, 10.8 mmol) was added into the mixture. The mixture was stirred at room temperature for 12 hours. After complication, the mixture was washed with (H₂O, 5% NaHCO₃, brine), and dried with MgSO₄, and solvent was removed. The crude product was purified by column chromatography to give 2.0 g compound 14, yield 72%.

Step15: Synthesis of compound 18

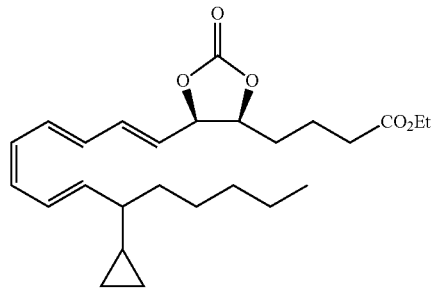

18

The compound 17 (3.3 g, 12.9 mmol) was dissolved in THF (25 mL) cooled to −78° C., and lithium diisopropylamide (1.65 g, 15.4 mmol) was added. The mixture was stirred for 30 min, and wormed to the room temperature. Then, hexamethylphosphoramide (2.77 g, 15.4 mmol) and compound 9 were added. The mixture was stirred at room temperature overnight. The mixture was added to an ice-cold solution of 2M aqueous HCl (150 mL). The mixture was extracted twice with ethyl acetate and the combined organic phases were washed twice with saturated aqueous NaCl solution, dried (MgSO$_4$), filtered, and concentrated to obtain crude product, and purified with flash chromatography to obtain 3.55 g compound 18, yield: 63%.

Step16: Synthesis of compound 19

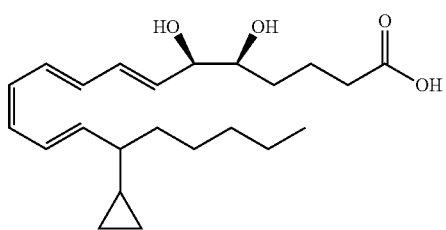

The compound 18 (1.46 g, 3.4 mmol) was dissolved in methanol (20 mL), 2 M sodium hydroxide was added into the solution, and the mixture was stirred at room temperature for 15 hours. After completion, adjusted the pH to 5, and the desired product compound 19 was precipitated 800 mg, yield: 62%.

What is claimed is:

1. A method for producing a compound of Formula 19, comprising:

contacting a ethyl propiolate with a lithium bromide base in the presence of HOAC in CH$_3$CN to obtain the compound of Formula 2;

contacting a compound of Formula 3 with n-Buli bromocyclane in THF to obtain a compound of Formula 4;

contacting the compound of Formula 4 with HZrCp$_2$Cl in THF to obtain a compound of Formula 5;

contacting the compound of Formula 2 with the compound of Formula 4 in the presence of Pd(PPH$_3$)$_2$Cl$_2$, DIBAH and ZnCl$_2$ to obtain a compound of Formula 6;

contacting the compound of Formula 6 with DIBAL in DCM to obtain a compound of Formula 7;

contacting the compound of Formula 7 with CBr$_4$, PPh$_3$, imidazole in DCM to obtain a compound of Formula 8;

contacting the compound of Formula 8 with P(OMe)$_3$ in CH$_3$CN to obtain a compound of Formula 9;

contacting the compound of Formula 10 with acetyl chloride in MeOH under room temperature to obtain a compound of formula 11;

contacting compound of Formula 11 with CDI in CH$_3$CN under a condition of refluxing to obtain a compound of Formula 12;

contacting the compound of Formula 12 with HCL in a mixture of Dioxane and water under a condition of refluxing to obtain a compound of Formula 13, wherein the volume ratio of Dioxane to water is about 3:1;

contacting the compound of Formula 13 with Ph$_3$PCHCO$_2$ and Benzolic acid in toluene under a condition of refluxing to obtain a compound of Formula 14;

contacting the compound of Formula 14 with H$_2$ in the presence of Pd/C in EtOH to obtain a compound of Formula 15;

contacting the compound of Formula 15 with DCC, and Cl$_2$CHCOOH to obtain a compound of Formula 16;

contacting the compound of Formula 16 with Ph3P=CHCHO in DCM to obtain a compound of Formula 17;

contacting the compound of Formula 17 with the compound of Formula 9 in the presence of LDA and HMPA in THF to obtain a compound of Formula 18;

contacting the compound of Formula 18 with NaOH in MeOH to obtain the compound of Formula 19

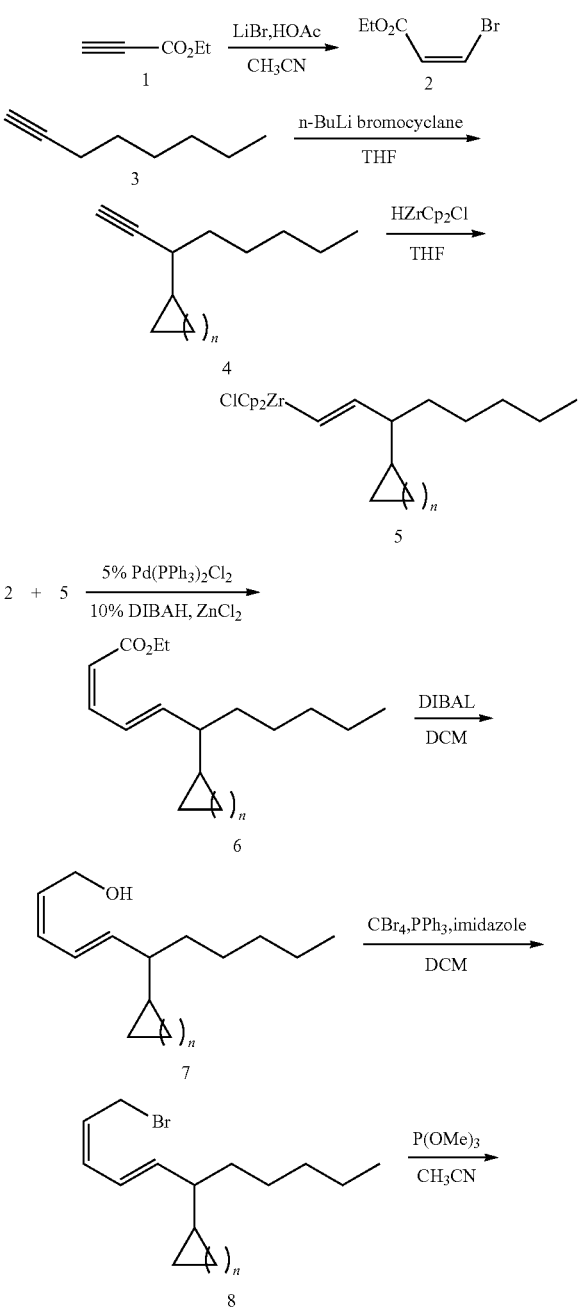

-continued
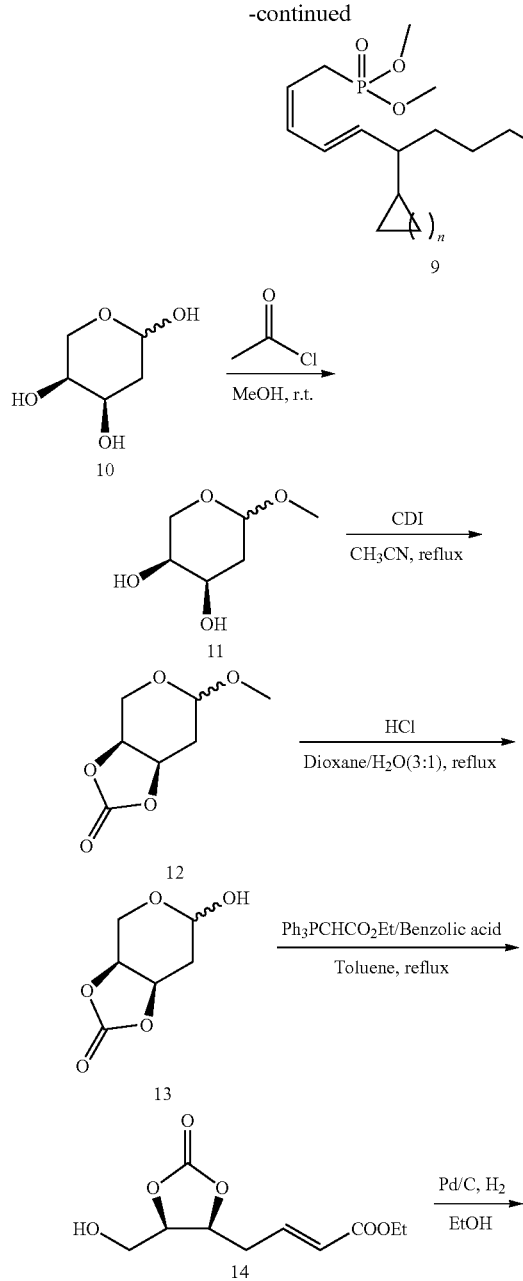
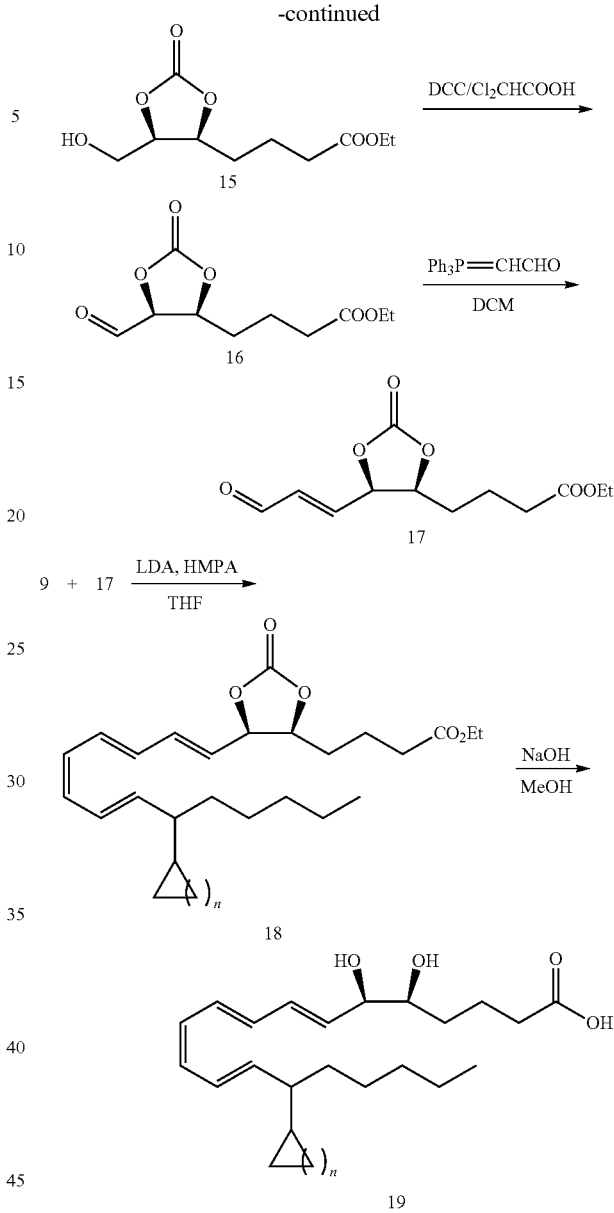
wherein n is an integer between 1 to 5.
* * * * *